United States Patent
Chong et al.

(10) Patent No.: US 6,544,198 B2
(45) Date of Patent: Apr. 8, 2003

(54) STETHOSCOPE SYSTEM FOR SELF-EXAMINATION USING INTERNET

(75) Inventors: Hoon Chong, 1136-1 Bono 3-Dong, Ansan-si, Kyeonggi-do (KR), 425-818; Jong Gie Kim, Seoul (KR)

(73) Assignees: Hoseo University, Asan-si (KR); Hoon Chong, Ansan-si (KR)

( * ) Notice: Subject to any disclaimer, the term of this patent is extended or adjusted under 35 U.S.C. 154(b) by 0 days.

(21) Appl. No.: 09/891,253

(22) Filed: Jun. 27, 2001

(65) Prior Publication Data

US 2002/0188227 A1 Dec. 12, 2002

(30) Foreign Application Priority Data

Jun. 11, 2001 (KR) .............................. 01-32499

(51) Int. Cl.[7] ................................. A61B 7/00
(52) U.S. Cl. ................. 600/586; 600/573; 600/300
(58) Field of Search ................. 600/586, 300, 600/573

(56) References Cited

U.S. PATENT DOCUMENTS

| | | | | |
|---|---|---|---|---|
| 5,619,991 A | * | 4/1997 | Sloane | 128/630 |
| 5,851,186 A | * | 12/1998 | Wood et al. | 600/437 |
| 6,014,432 A | * | 1/2000 | Modney | 379/106.02 |
| 6,304,788 B1 | * | 10/2001 | Eady et al. | 700/86 |

* cited by examiner

Primary Examiner—Tony M. Argenbright
Assistant Examiner—Johnny H. Hoang
(74) Attorney, Agent, or Firm—Jacobson Holman PLLC

(57) ABSTRACT

A stethoscope system for self-examination whereby the condition of health of a particular individual can be diagnosed by comparing characteristic sound waves classified by diseases with sound waves generated from various parts of the individual's body. This system also provides for remote medical examination whereby sound waves generated from various parts of the individual's body are transmitted to a medical specialist using the internet and receiving a virtual medical examination via the internet.

5 Claims, 7 Drawing Sheets

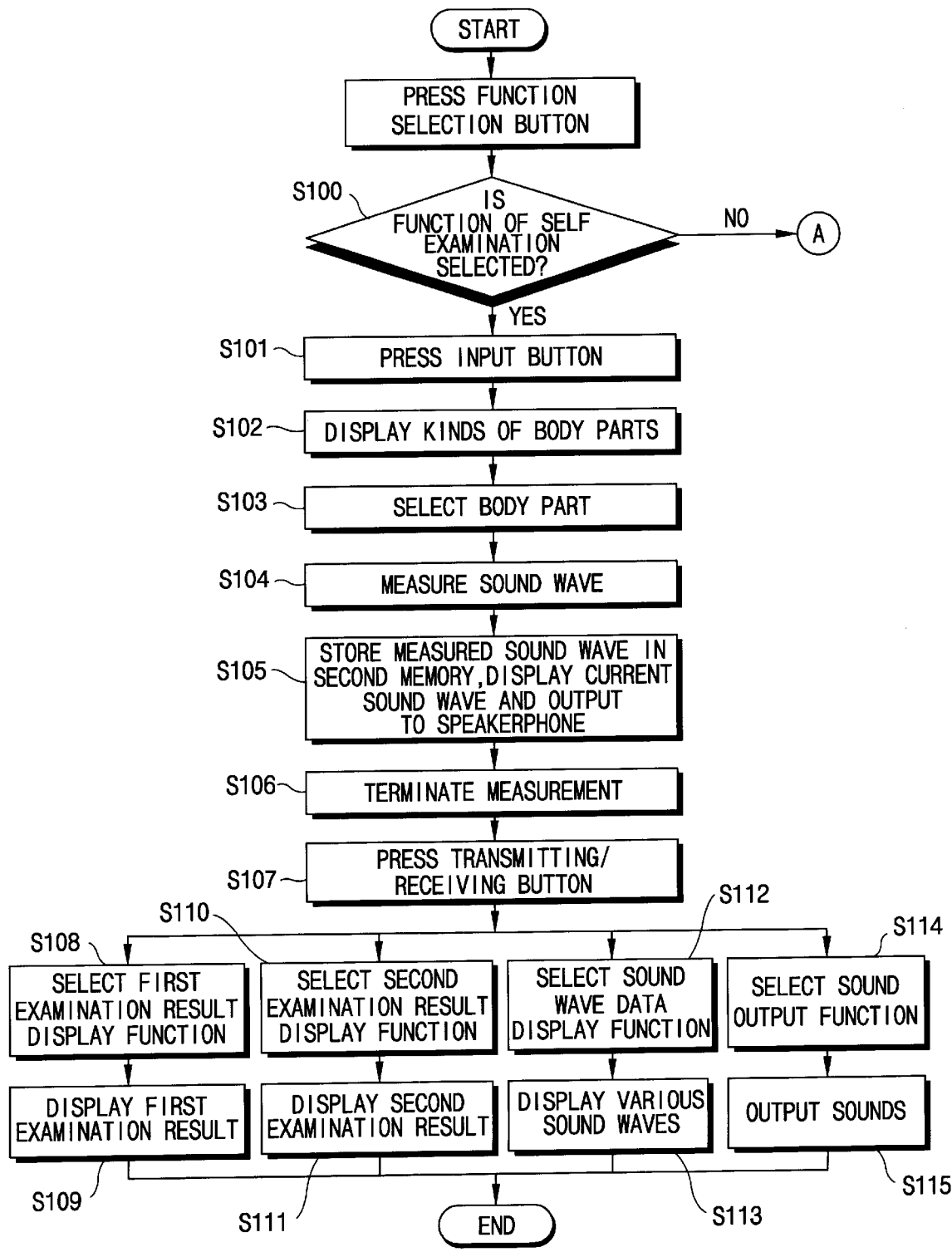

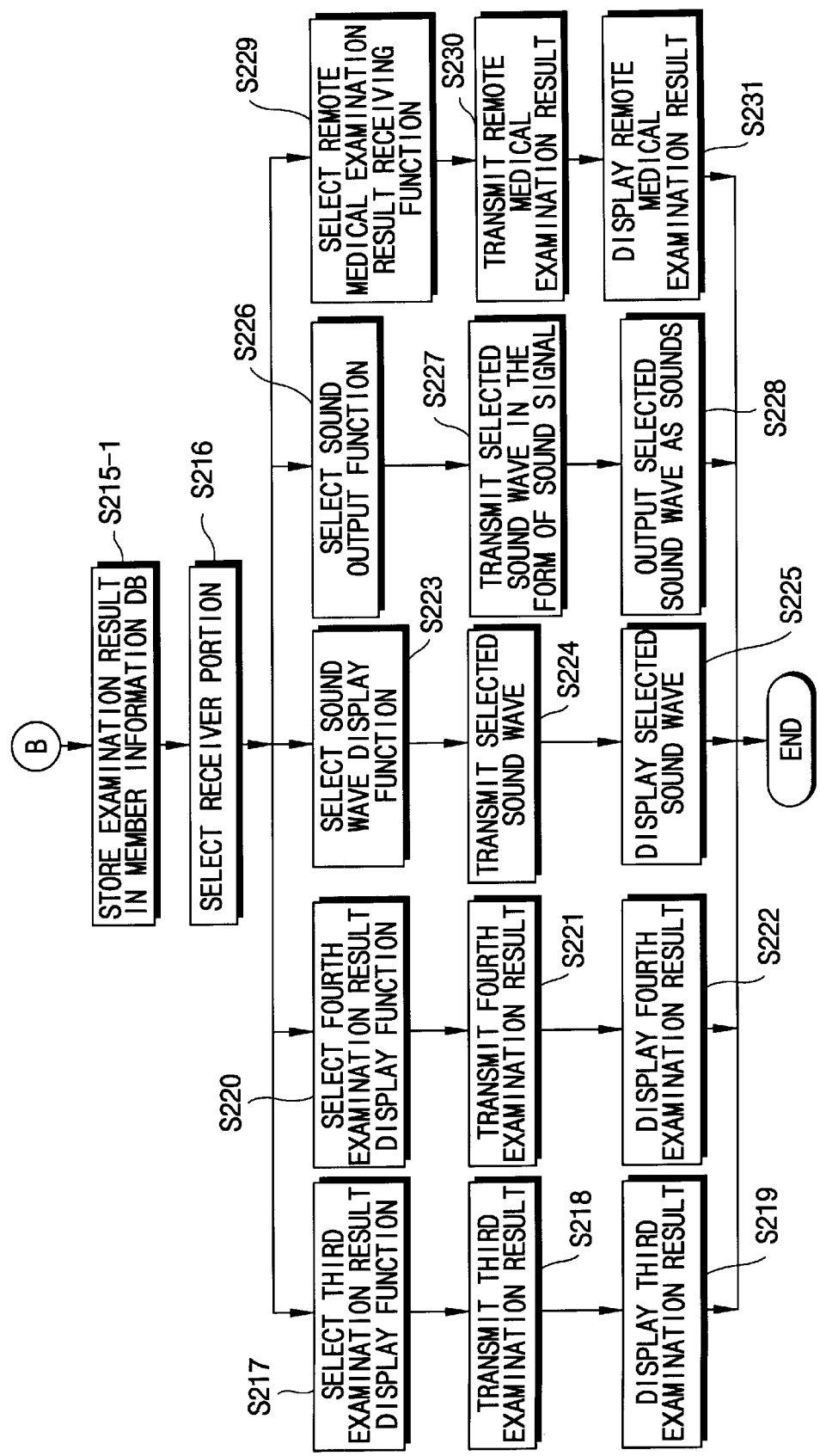

STETHOSCOPE SYSTEM FOR SELF-EXAMINATION USING INTERNET

BACKGROUND OF THE INVENTION

1. Field of the Invention

The present invention relates to a stethoscope system for self-examination using an Internet. More particularly, the present invention relates to a digital stethoscope system, which can diagnose the health condition of a patient by comparing a characteristic sound wave of a disease occurring in the body of a patient with a stethoscopic sound wave.

2. Description of the Related Art

In a conventional stethoscope, another physician(s) except an attending physician cannot auscultate, or hear, a patient's breathing sound directly by use of the stethoscope, resulting in different diagnoses according to the physician's experience or subjectivity. Also, patients cannot hear the sound generated from their own bodies. Since the sound heard by the physician cannot be stored but are recorded in medical terms, it is not possible to objectively monitor a change in the patient's condition. In the field of medical education, since students cannot hear the patient's breathing sound simultaneously, the students cannot confidently diagnose the patient's condition from the sound heard by the students themselves. Also, professors who are physicians, cannot accurately evaluate the students' determination because they cannot auscultate parts of the patient's body at the same time as the students. In accordance with recent development of remote medical examination using the Internet or information highway, exchange of stethoscopic sounds is indispensable. However, it is not possible to transmit a stethoscopic sound to a physician in a remote area by use of the conventional stethoscope. Also, since it is not possible to analyze the stethoscopic sound and to compare the stethoscopic sound with a characteristic sound of a disease, ordinary people other than physicians cannot use the stethoscope easily.

SUMMARY OF THE INVENTION

It is an object of the present invention to provide a stethoscope system for self-examination, by which the health condition of a particular individual can be diagnosed by comparing characteristic sound waves classified by diseases with sound waves generated from various parts of the individual's body.

It is another object of the present invention to provide a remote medical examination system, by which sound waves generated from various parts of a particular individual's body are transmitted to a medical specialist in a remote area using the Internet for remote medical examination.

To accomplish the above object of the present invention, there is provided a stethoscope system for self-examination using the Internet, the stethoscope system including a member's digital stethoscope for measuring sound waves of various parts of a member's body, connecting to a prescribed web address in accordance with the member's instruction, transmitting the member's current sound wave data, requesting for remote medical examination, and displaying an examination result input from the outside, a web server for storing the measured current sound wave data in a current sound wave database in response to the member's request if the measured current sound wave data is received from the member's digital stethoscope, examining the member's health condition using the measured current sound wave data, disease sound wave data pre-stored in a disease sound wave database, and the normal sound wave data pre-stored in a normal sound wave database, connecting to the member's digital stethoscope for transmission of the examination result, or transmitting member identification information, details for the request for remote medical examination, the member's current sound wave data and the pre-stored member's normal sound wave data to request a medical specialist for remote medical examination, a remote medical examination system for receiving the member identification information, details for the request for remote medical examination, the member's current sound wave data and the pre-stored member's normal sound wave data from the web server, performing remote medical examination by the medical specialist based on the received data, and transmitting the examination result to the web server by the medical specialist's instruction, and a communication system for connecting the member's digital stethoscope, the web server and the remote medical examination system with one another.

Also, the member's digital stethoscope may include a sound tube for collecting sounds originated from various parts of the body, a microphone through which the collected sounds are input, a signal processor for digitally processing the signal input through the microphone, a first memory in which the operating program of the digital stethoscope is stored, a second memory in which the current sound wave data measured through the sound tube are classified by parts of the body and stored, an input button for instructing the measured sound waves to be input and specifying the storage location thereof, a transmitting/receiving button for instructing the measured sound waves to be transmitted and requesting the transmission of an examination result, a display portion for displaying the measured sound waves, disease sound waves and the examination result in accordance with the instruction of the transmitting/receiving button, and a controller operating by the operating program, for storing the measured sound waves at a predetermined location of the second memory according to the state of the input button, transmitting the measured sound waves of the second memory to the web server according to the state of the transmitting/receiving button, and receiving the examination result from the web server to be displayed on the display portion.

The communication system for connecting the member's digital stethoscope and the web server is preferably a wireless mobile communication system.

Also, the communication system for connecting the member's digital stethoscope and the web server is preferably a wired communication system.

According to another aspect of the present invention, there is provided a digital stethoscope including a sound tube for collecting sounds originated from various parts of the body, a microphone through which the collected sounds are input, a signal processor for digitally processing the signal input through the microphone, a first memory in which the operating program of the digital stethoscope is stored, a second memory in which the measured sound wave data by parts of the body output in the form of a digital signal from the signal processor is stored, a third memory in which disease sound wave data is stored, an input button for instructing the measured sound waves to be input and specifying the storage location thereof, an output button for instructing the measured sound waves, diseases sound waves and examination result to be output, a speakerphone for outputting the measured sound waves, diseases sound waves and examination result in the form of sound signals, a display portion for displaying the measured sound waves, disease sound waves and the examination result in accordance with the instruction of the output button, and a controller operating by the operating program, for storing the measured sound waves at a predetermined location of the second memory according to the state of the input button, sequentially outputting the disease sound waves of the third memory to the speakerphone or the display portion according to the state of the output button, and checking whether there is disease sound waves similar to the measured sound waves to extract the examination result regarding the presence or absence of a disease in the examined body to be output to the speakerphone or display portion.

BRIEF DESCRIPTION OF THE DRAWINGS

The above object and advantages of the present invention will become more apparent by describing in detail a preferred embodiment thereof with reference to the attached drawings in which:

FIG. 5 is a flow chart of self-examination using only the digital stethoscope according to the present invention;

FIGS. 6A and 6B are flow charts of remote medical examination using a digital stethoscope using the Internet according to the present invention.

DESCRIPTION OF THE PREFERRED EMBODIMENT

A preferred embodiment of the present invention will now be described in detail with reference to the accompanying drawings.

Figure 1:
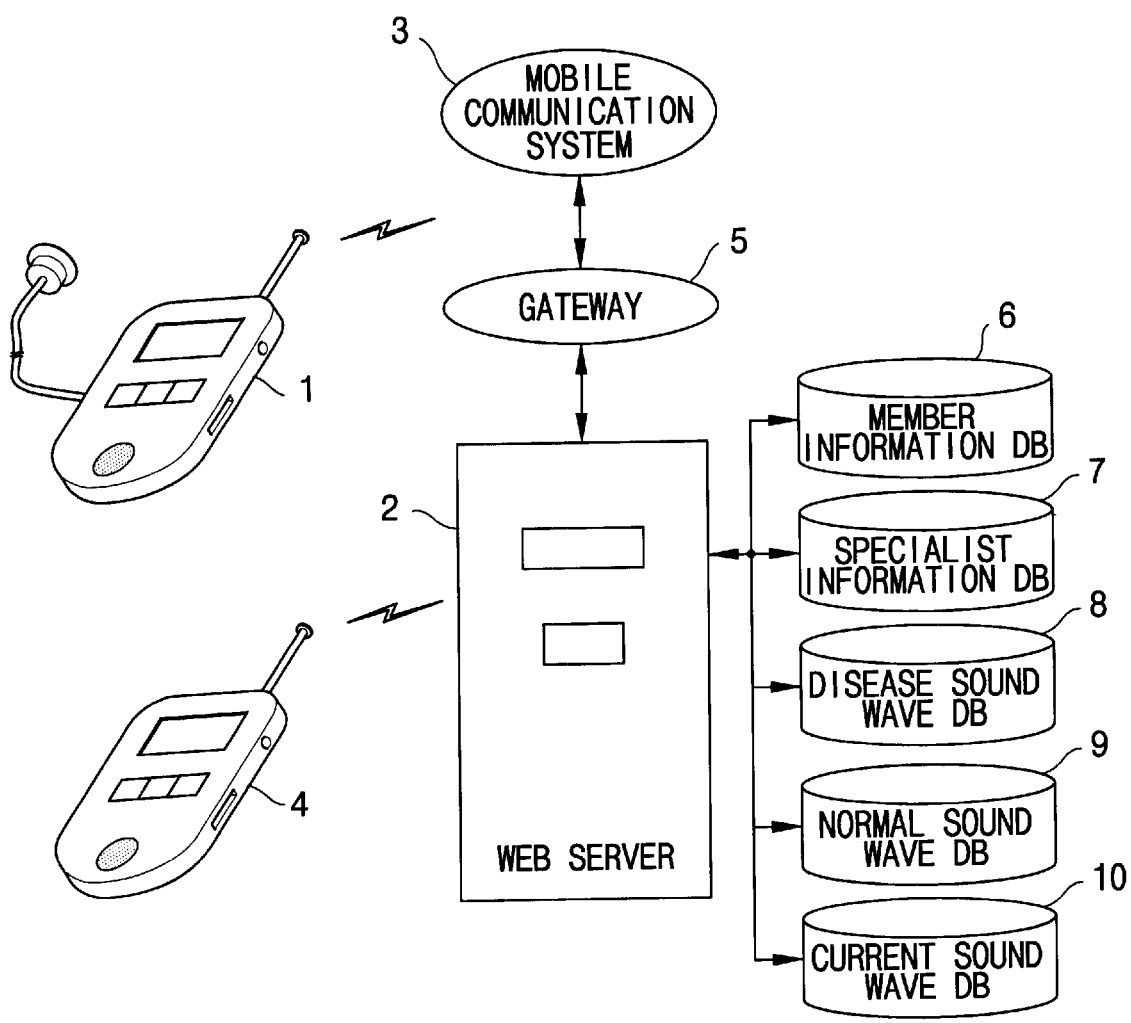
FIG. 1 is a schematic diagram showing a preferred embodiment of a stethoscope system for self-examination using a mobile communication network according to the present invention.

FIG. 1 is a schematic diagram showing a preferred embodiment of a stethoscope system for self-examination using a mobile communication network according to the present invention, including a member's digital stethoscope 1, a web server 2 for providing mobile communication services, a mobile communication network 3 and a remote medical examination system 4. The web server 2 includes a member information database 6 in which data necessary for authentication of members, members' health condition and remote medication examination results are stored, a specialist information database 7 in which information on specialists is stored, a diseases sound wave database 8 in which sound wave data by disease is stored, a normal sound wave database 9 in which the data of sound waves measured from members being in a normal state based on the specialist's determination, is stored, and a current sound wave database 10 in which the data of current sound waves measured at the time of examination of members' health conditions is stored. The web server 2 is connected with the mobile communication network 3 through a gateway 5.

In the stethoscope system having the above-described configuration, the member's digital stethoscope 1 measures sound waves of various parts of a member's body and transmits the member's current sound wave data to the web server 2. The web server 2 analyzes the member's health condition from the member's current sound wave data and the disease sound wave data using an examination-purpose computer program. Alternatively, in response to the member's request for remote medical examination through the member's digital stethoscope 1, the web server 2 may transmit the request for the remote medical examination to the remote medical examination system 4, so that a medical specialist can perform remote medical examination by means of the remote medical examination system 4.

In the case of using the mobile communication network, the remote medical examination system 4 preferably includes a mobile communication terminal, such as a cellular phone, a Personal Digital Assistant (PDA), a Personal Communication Services (PCS) terminal, an International Mobile Telecommunication-2000 (IMT-2000) terminal and so on.

The web server 2 sends the examination result originated from the computer program or the medical specialist in a remote area back to the member's digital stethoscope 1, thereby offering accurate information on the member's health condition.

In order for a plurality of users to use the system according to the present invention, they must gain membership by connecting to the web server 2 and entering information necessary for member enrollment when or before using the system. When enrolling, the users preferably enter not only basic personal data but also accurate data for determining the health condition including physical constitution or clinical history. Then, the web server 2 stores the information on the member in the member information database 6 so as to allow the medical specialist to accurately diagnose the member's health condition at the time of remote medical examination.

Figure 2:
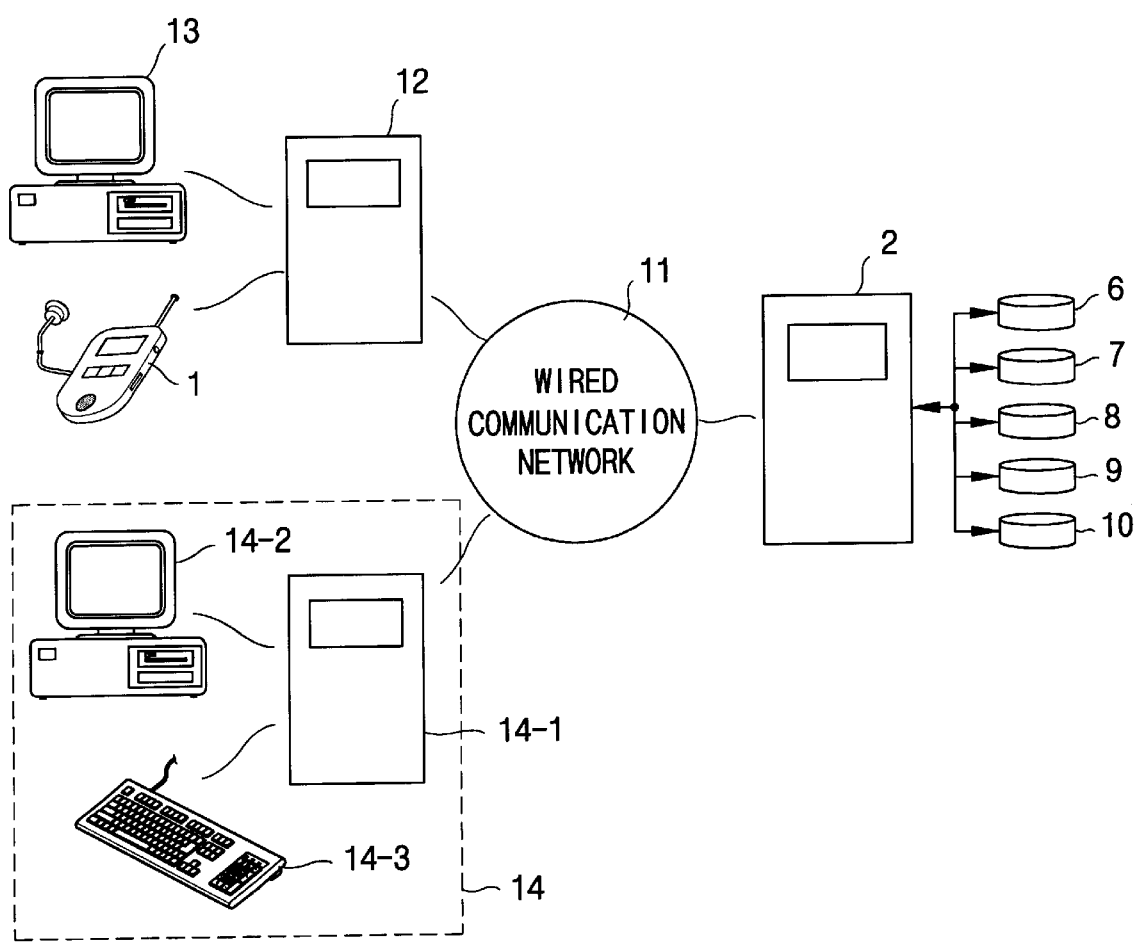
FIG. 2 is a schematic diagram showing a preferred embodiment of a stethoscope system for self-examination using a wired communication network according to the present invention.

FIG. 2 is a schematic diagram showing a preferred embodiment of a stethoscope system for self-examination using a wired communication network according to the present invention, including a member's digital stethoscope 1, a member's computer 12, a monitor 13 connected to the member's computer 12, a remote medical examination system 14, a web server 2, and a plurality of databases 6 through 10 connected to the web server 2. The member's computer 12, the remote medical examination system 14 and the web server 2 are connected through a wired communication network 11.

Also, the remote medical examination system 14 includes a specialist's computer 14-1, a monitor 14-2 connected to the specialist's computer 14-1, and a key board 14-3 connected to the specialist's computer 14-1, for inputting specialist's instruction.

In the stethoscope system for self-examination using the wired communication network 11, the member measures the sound wave data from various parts of his/her body using the member's digital stethoscope 1 connected to the member's computer 12 and transmits the measured sound wave data to the web server 2 via the member's computer 12 connected to a wired communication network 11. When the member requests for remote medical examination through the member's digital stethoscope 1, the request is transmitted to the web server 2 via the member's computer 12. Then, the web server 2 transmits the request to the remote medical examination system 14, so that the medical specialist in a remote area can perform remote medical examination.

Preferably, the member's stethoscope 1 and the remote medical examination system 4, as shown in FIG. 1, are integrally connected to a transmission system such as a cellular phone, an external ordinary telephone connected by cable, or a video transmission system such as an IMT-2000 terminal, thereby performing remote medical examination while the member and the medical specialist communicate with each other in real-time.

Also, as shown in FIG. 2, the member's computer 12 and the specialist's computer 14-1 may be configured such that they are connected to an external telephone device or a video transmission system such as an IMT-2000 terminal by a connection cable to perform remote medical examination through the web server 2, and remote medical examination can also be performed while the member and the medical specialist communicate with each other in real-time through the external telephone device or video transmission system such as an IMT-2000 terminal.

Figure 3:
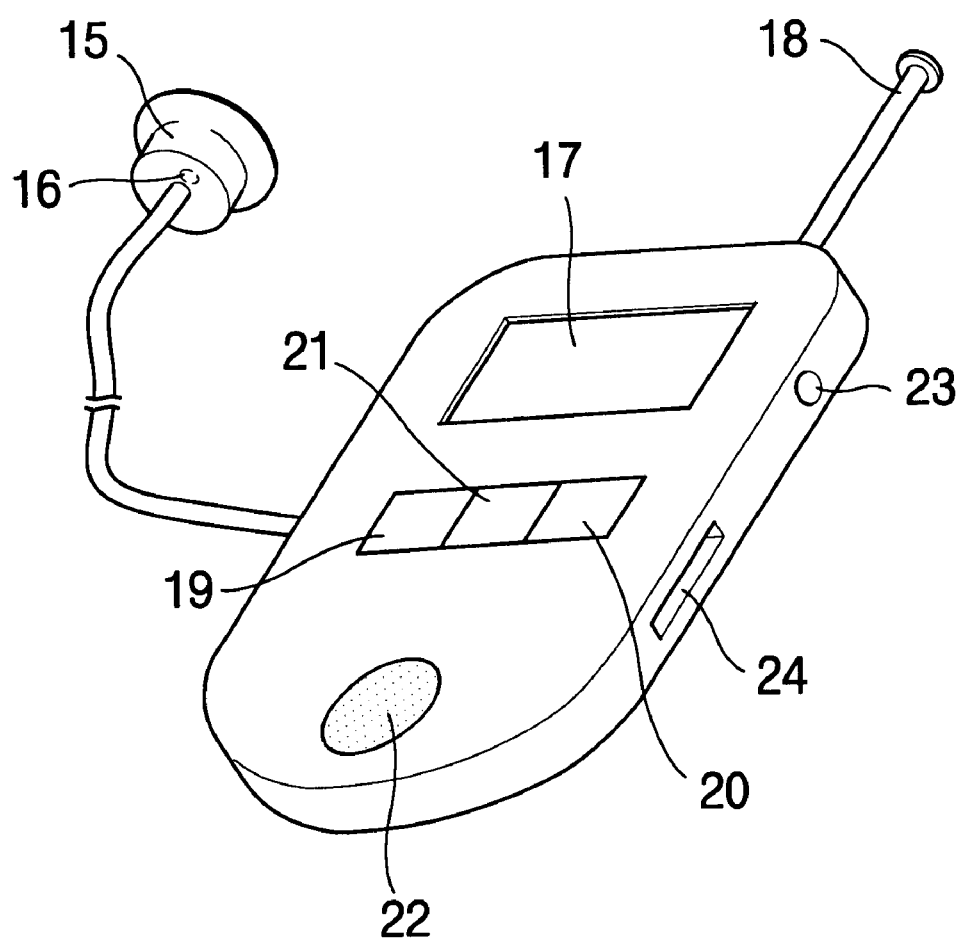
FIG. 3 is an outer perspective view of a digital stethoscope according to the present invention.

FIG. 3 is an outer perspective view of a digital stethoscope according to the present invention. The digital stethoscope according to the present invention includes a sound tube 15 for collecting sounds originated from various parts of the body, a microphone 16 through which the collected sounds are input, a display portion 17 for displaying various sound waves and examination results, a transmitting/receiving antenna 18 necessary for wireless communication through a mobile communication system, an input button 19 for storing sound waves measured from various parts of the body and input through the sound tube 15 at a predetermined location, a transmitting/receiving button 20 for receiving member's instruction regarding transmission/reception from the digital stethoscope, a function selection button 21 for selecting either a function of self-examination using the digital stethoscope or a function of remote medical examination by connecting the digital stethoscope with a communication network, a speakerphone 22 for outputting the measured sound wave data as a sound, an earphone terminal 23 for being connected with an earphone, and a signal input/output terminal 24 for connecting the digital stethoscope with a computer.

Figure 4:
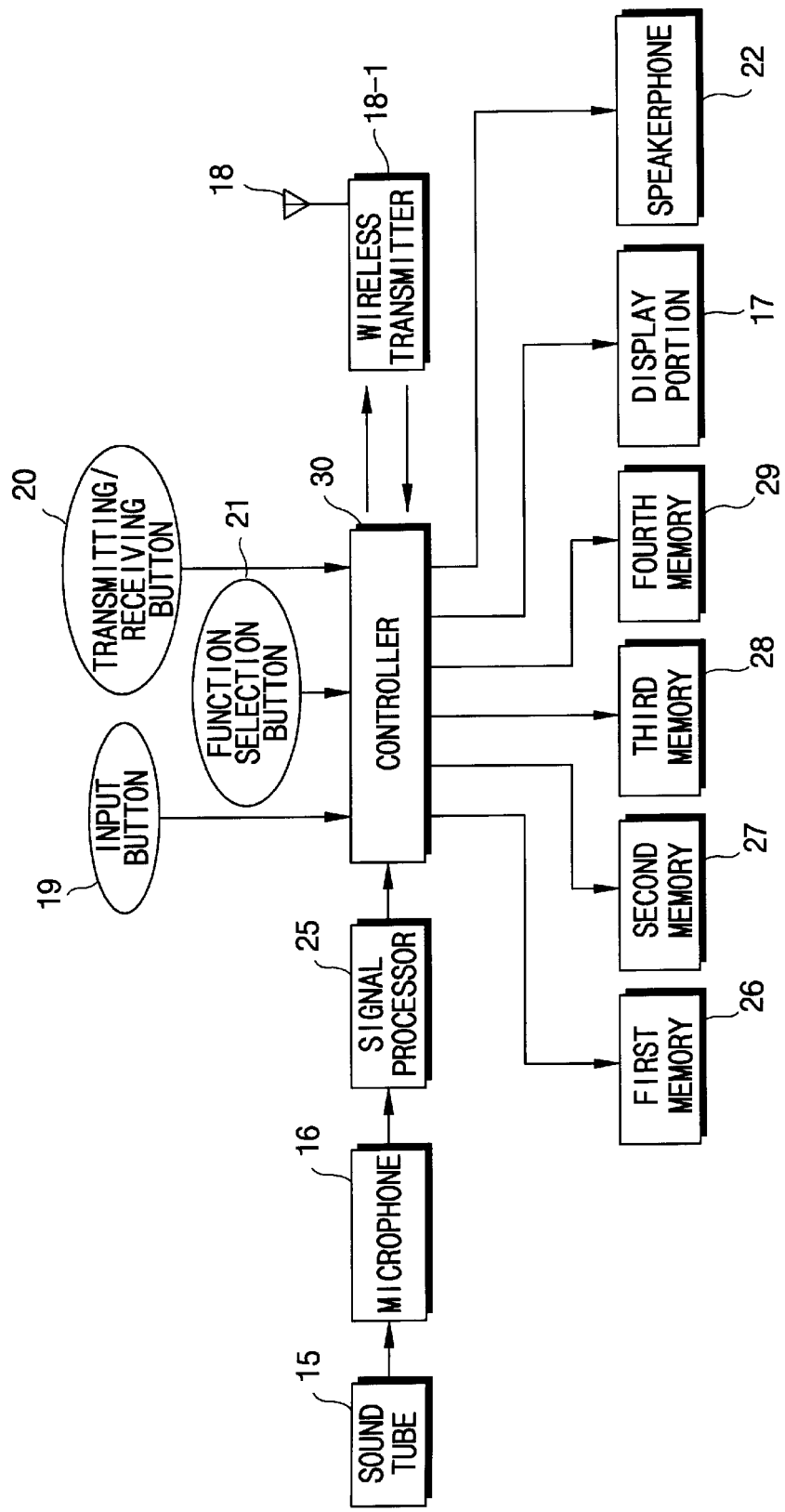
FIG. 4 is a block diagram showing a preferred embodiment of the digital stethoscope according to the present invention.

FIG. 4 is a block diagram showing a preferred embodiment of the digital stethoscope according to the present invention, including a sound tube 15 for collecting sounds originated from various parts of the body, a microphone 16 through which the collected sounds are input, a signal processor 25 for digitally processing the signal input through the microphone 16, a first memory 26 in which the operating program of the digital stethoscope is stored, a second memory 27 in which the current sound wave data measured through the sound tube 15 are classified by parts of the body, and stored, a third memory 28 in which the sound wave data by disease are stored, a fourth memory 29 in which the normal sound wave data measured when the member's health condition is determined to be normal based on the specialist's determination, a display portion 17 for displaying various sound waves and examination results, and a speakerphone 22 for outputting the measured sound wave data as a sound.

Also, the digital stethoscope according to the present invention includes an input button 19 for storing the current sound wave data for a particular part of the body, the data input through the sound tube 15 and the microphone 16 at a predetermined location, a transmitting/receiving button 20 for causing the examination result of the member's health condition analyzed from the current sound wave data and disease sound wave data to be displayed on the display portion 17 and receiving various sound wave data and examination result respectively transmitted from the web server 2 and the remote medical examination system 4 as shown in FIG. 1, a function selection button 21 for selecting either a function of remote medical examination by connecting the member's digital stethoscope with a communication network or a function of self-examination using only the digital stethoscope, a wireless transmitter/receiver 18-1 for converting the electrical digital data output from a controller 30 into a radio signal to transmit the same to the web server 2 or converting the received radio signal into an electrical digital signal and transmitting the same to the controller 30, and the controller 30 operating by the operating program stored in the first memory 26 for controlling the operation of the member's digital stethoscope. Also, the member's digital stethoscope may include an earphone terminal 23 for being connected with an earphone, and a signal input/output terminal 24 for connecting the digital stethoscope with a wired communication network. By means of the function selection button 21, the controller 30 determines whether self-examination is to be performed using only the digital stethoscope or remote medical examination is to be performed by connecting the member's digital stethoscope to the web server 2 and the remote medical examination system 4 by the mobile communication system 3.

In the case of performing self-examination using only the digital stethoscope, according to the state of the input button 19, the controller 30 causes the current sound wave data input through the sound tube 15 to be stored at a predetermined location of the second memory 27 or the current sound wave data to be stored in the fourth memory 29 when the member's health condition is determined by the medical specialist to be normal. Also, according to the state of the transmitting/receiving button 20, the controller 30 causes the current sound wave data, the disease sound wave data and the normal sound wave data to be displayed on the display portion 17 or to be output as a sound through the speakerphone 22. Also, the controller 30 analyzes the health condition from the current sound wave data, the disease sound wave data and the normal sound wave data by using the operating program, and displays the examination result on the display portion 17.

Otherwise, in the case of performing remote medical examination by connecting the member's digital stethoscope to the web server 2 and the remote medical examination system 4 by the mobile communication system 3, according to the state of the input button 19, the controller 30 causes the current sound wave data input through the sound tube 15 to be stored at a predetermined location of the second memory 27 or the current sound wave data to be stored in the fourth memory 29 when the member's health condition is determined by the medical specialist to be normal. Also, according to the state of the transmitting/receiving button 20, the controller 30 causes the current sound wave data to be transmitted to the web server 2 through the wireless transmitter/receiver 18-1 so that the web server 2 stores the received current sound wave data in the current sound wave database 10.

The current sound wave data, the disease sound wave data and the normal sound wave data are analyzed by the examination-purpose computer program provided in the web server 2, and the web server 2 transmits the analyzed examination result for the member's health condition to the wireless transmitter/receiver 18-1 through the mobile communication system 3.

When the member requests for medical specialist identification information and remote medical examination by means of the transmitting/receiving button 20, the controller 30 transmits details of the request for the medical specialist identification information and remote medical examination to the web server 2 through the wireless transmitter/receiver 18-1. The web server 2 searches for the address matched with the medical specialist identification information from the specialist information database 7, and transmits the member identification information, the details of the member's request for remote medical examination, the member's current sound wave data and normal sound wave data to the remote medical examination system 4. Then, the medical specialist can perform remote medical examination from the member identification information, the details of the member's request for remote medical examination, the member's current sound wave data and normal sound wave data by means of the remote medical examination system 4.

FIG. 5 is a flow chart of self-examination using only the digital stethoscope according to the present invention. Referring to FIG. 5, the procedure of performing self-examination by measuring sound waves of various parts of the body using the digital stethoscope according to the present invention will now be described in detail.

First, if a member uses the function selection button 21 to select a function of self-examination using the member's digital stethoscope 1 (step S100), and then the member presses the input button 19 (step S101), the controller 30 processes the display portion 17 of the member's digital stethoscope 1 to display items of various parts of the body so that the member selects a part to be measured (step S102). Then, a part among the parts displayed in step S102 is selected (step S103). The sound tube 15 of the member's digital stethoscope 1 is moved to the selected part to measure sound waves (step S104), which are then stored in a predetermined location of the second memory 27, and simultaneously the current sound wave data is displayed on the display portion 17 and output as a sound through the speakerphone 22 (step S105). The step S105 is continuously performed until an instruction of measurement termination is initiated (step S106). Here, initiating the instruction of measurement termination in step S106 can be embodied in various manners, including member's pressing the input button 19 or providing a separate input termination key.

After terminating the measurement in step S106, if the transmitting/receiving button 20 is pressed for the purpose of confirming the examination result, the controller 30 processes various menu items to be displayed on the display portion 17 for member's selection (step S107). The menu items displayed in step S107 include a first examination result display function of displaying an examination result obtained by analyzing the current sound wave data and the disease sound wave data by the operating program stored in the first memory 26, a second examination result display function of displaying an examination result obtained by analyzing the current sound wave data and the normal sound wave data, a sound wave display function of displaying the current sound wave data, the disease sound wave data and the normal sound wave data according to the member's option, and a sound output function of selectively outputting the current sound wave data, the disease sound wave data and the normal sound wave data as a sound.

If the first examination result display function among the menu items displayed on the display portion 17 is selected (step S108), the examination result obtained by analyzing the current sound wave data and the disease sound wave data by the operating program is displayed on the display portion 17 (step S109). If the second examination result display function is selected (step S110), the examination result obtained by analyzing the current sound wave data and the normal sound wave data is displayed on the display portion 17 (step S111). If the sound wave display function is selected (step S112), the current sound wave data, the disease sound wave data and the normal sound wave data are simultaneously or individually displayed on the display portion 17 as waveforms, according to the member's option (step S113). If the sound output function is selected (step S114), the current sound wave data, the disease sound wave data and the normal sound wave data are selectively output as a sound through the speakerphone 22 (step S115).

Figure 6A:
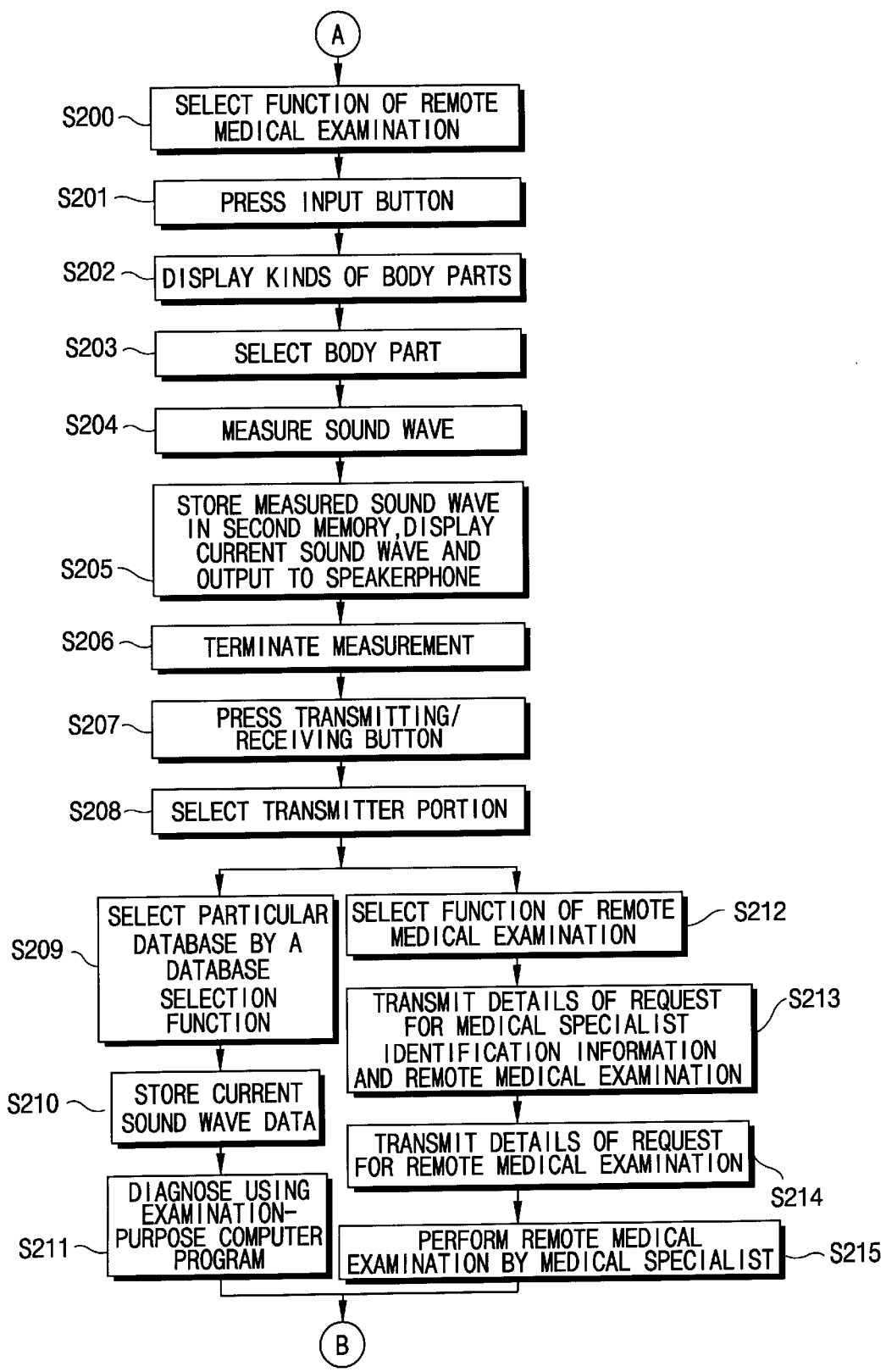

FIGS. 6A and 6B are flow charts of remote medical examination using a digital stethoscope using the Internet according to the present invention. Referring to FIGS. 6A and 6B, the procedure of performing remote medical examination by measuring sound waves of various parts of the body using the digital stethoscope according to the present invention will now be described in detail.

First, if a member connects to the web server 2, enters information for member authentication to log in, and then selects the function selection button 21 to select a function of remote medical examination using the member's digital stethoscope 1 (step S200), and then the member presses the input button 19 (step S201), the controller 30 processes the display portion 17 of the member's digital stethoscope 1 to display items of various parts of the body so that the member selects a part to be measured (step S202). Then, a part among the parts displayed in step S202 is selected (step S203). The sound tube 15 of the member's digital stethoscope 1 is moved to the selected part to measure sound waves (step S204), which are then stored in a predetermined location of the second memory 27, and simultaneously the current sound wave data is displayed on the display portion 17 and output as a sound through the speakerphone 22 (step S205). The step S205 is continuously performed until an instruction of measurement termination is initiated (step S206). Here, initiating the instruction of measurement termination in step S206 can be embodied in various manners, including member's pressing the input button 19 or providing a separate input termination key.

After terminating the measurement in step S206, if the transmitting/receiving button 20 is pressed, the controller 30 processes various menu items to be displayed on the display portion 17 for member's selection (step S207). The menu items displayed in step S207 include a transmitter portion and a receiver portion. The menu items of the transmitter portion include a database selection function for storing sound wave data and a remote medical examination selection function. The menu items of the receiver portion include a third examination result display function of displaying an examination result obtained by analyzing the current sound wave data and the disease sound wave data by the examination-purpose operating program stored in the web server 2, a fourth examination result display function of displaying an examination result obtained by analyzing the current sound wave data and the normal sound wave data, a sound wave display function of displaying the current sound wave data, the disease sound wave data and the normal sound wave data according to the member's option, a sound output function of selectively outputting the current sound wave data, the disease sound wave data and the normal sound wave data as a sound, and a remote medical examination receiving function of receiving the specialist's remote medical examination result.

If the member selects the transmitter portion among the menu items displayed on the display portion (step S208) to select a particular database, for example, a current sound wave database, by a database selection function (step S209), the web server 2 causes the current sound wave data stored in the second memory 27 of the member's digital stethoscope 1 to be stored at a predetermined location of the selected database (step S210). Thereafter, the information stored in the selected database is analyzed using the examination-purpose computer program provided in the web server 2 to examine the member's health condition (step S211), and the examination result is stored in the member information database 6 (step S215-1). Then, the member selects the remote medical function (step S212) and enters details of the request for medical specialist identification information and remote medical examination to transmit the same to the web server 2 (step S213). The web server 2 transmits the member identification information, the details of the member's request for remote medical examination, the member's current sound wave data and normal sound wave data to the remote medical examination system 4 (step S214), so that the medical specialist can perform remote medical examination (step S215), and the examination result is stored in the member information database 6 by the medical specialist's instruction (step S215-1). The remote medical examination result may be transmitted directly to the member's digital stethoscope 1 via the web server 2 through the remote medical examination system 4 by the medical specialist.

After the transmission, if the member selects the receiver portion among the menu items for the purpose of receiving the examination result (step S216) to select the third examination result display function (step S217), the web server 2 transmits an examination result obtained by analyzing the current sound wave data and the disease sound wave data by the examination-purpose computer program to the member's digital stethoscope 1 through the mobile communication system 3 (step S218). The member's digital stethoscope 1 receives the third examination result to be displayed on the display portion 17 (step S219). If the member selects the fourth examination result display function (step S220), the web server 2 transmits an examination result obtained by analyzing the current sound wave data and the normal sound wave data to the member's digital stethoscope 1 through the mobile communication system 3 (step S221). The member's digital stethoscope 1 receives the fourth examination result to be displayed on the display portion 17 (step S222). If the sound wave display function is selected (step S223), the web server 2 transmits one or more data among the current sound wave data, the disease sound wave data and the normal sound wave data to the member's digital stethoscope 1 through the mobile communication system 3 (step S224). Then, the member's digital stethoscope 1 receives the transmitted sound wave data to be displayed on the display portion 17 (step S225). If the sound output function is selected (step S226), the web server 2 sequentially transmits the current sound wave data, the disease sound wave data and the normal sound wave data one by one by a prescribed order through the mobile communication system 3 in the form of sound signals (step S227). Then, the member's digital stethoscope 1 receives the sound data of the transmitted sound signals and outputs the same through the speakerphone 22 (step S228).

If the member who has selected a remote medical examination function in step S212 selects a remote medical examination result receiving function after completing step S215 (step S229), the web server 2 transmits the remote medical examination result originated from the specialist whose information is stored in the member information database 6 to the member's digital stethoscope 1 (step S230). The member's digital stethoscope 1 receives the remote medical examination result to be displayed on the display portion 17 (step S231).

Alternatively, the remote medical examination according to the present invention is preferably performed such that the remote medical examination is performed by data transmission between a member and a medical specialist through a web server using a built-in telephone integrally connected with the member's digital stethoscope or an external telephone device connected with the member's digital stethoscope by a connecting cable and a telephone device connected to a remote medical examination system or a medical specialist's telephone device, while the member and the medical specialist communicate with each other in real-time.

According to the digital stethoscope of the present invention, the current sound waves of various parts of human body can be measured, and ordinary people other than medical specialists can easily examine their health conditions by the examination result obtained by comparing the measured sound wave data with the disease sound wave data pre-stored in the digital stethoscope and analyzing the same. Also, the digital stethoscope is connected with a web server through a mobile communication system so that the remote medical examination can be performed in real-time by a medical specialist using a specialist's digital stethoscope, that is, a remote medical examination system connected with the web server.

What is claimed is:

1. A stethoscope system for self-examination using the Internet, comprising:

a member's digital stethoscope for measuring sound waves of various parts of a member's body, connecting to a prescribed web address in accordance with the member's instruction, transmitting the member's current sound wave data, requesting for remote medical examination, and displaying an examination result input from the outside;

a web server for storing the measured current sound wave data in a current sound wave database in response to the member's request if the measured current sound wave data is received from the member's digital stethoscope, examining the member's health condition using the measured current sound wave data, disease sound wave data pre-stored in a disease sound wave database, and the normal sound wave data pre-stored in a normal sound wave database, connecting to the member's digital stethoscope for transmission of the examination result, or transmitting member identification information, details for the request for remote medical examination, the member's current sound wave data and the pre-stored member's normal sound wave data to request a medical specialist for remote medical examination;

a remote medical examination system for receiving the member identification information, details for the request for remote medical examination, the member's current sound wave data and the pre-stored member's normal sound wave data from the web server, performing remote medical examination by the medical specialist based on the received data, and transmitting the examination result to the web server by the medical specialist's instruction; and a communication system for connecting the member's digital stethoscope, the web server and the remote medical examination system with one another.

2. The stethoscope system according to claim 1, wherein the member's digital stethoscope comprises:

a sound tube for collecting sounds originated from various parts of the body;

a microphone through which the collected sounds are input;

a signal processor for digitally processing the signal input through the microphone;

a first memory in which the operating program of the digital stethoscope is stored;

a second memory in which the measured sound wave data by parts of the body output in the form of a digital signal from the signal processor is stored;

an input button for instructing the measured sound waves to be input and specifying the storage location thereof;

a transmitting/receiving button for instructing the measured sound waves to be transmitted and requesting the transmission of an examination result;

a display portion for displaying the measured sound waves, disease sound waves and the examination result in accordance with the instruction of the transmitting/receiving button; and a controller operating by the operating program, for storing the measured sound waves at a predetermined location of the second memory according to the state of the input button, transmitting the measured sound waves of the second memory to the web server according to the state of the transmitting/receiving button, and receiving the examination result from the web server to be displayed on the display portion.

3. The stethoscope system according to claim 1, wherein the communication system for connecting the member's digital stethoscope and the web server is a wireless mobile communication system.

4. The stethoscope system according to claim 1, wherein the communication system for connecting the member's digital stethoscope and the web server is a wired communication system.

5. A digital stethoscope comprising:

a sound tube for collecting sounds originated from various parts of the body;

a microphone through which the collected sounds are input;

a signal processor for digitally processing the signal input through the microphone;

a first memory in which the operating program of the digital stethoscope is stored;

a second memory in which the measured sound wave data by parts of the body output in the form of a digital signal from the signal processor is stored;

a third memory in which disease sound wave data is stored;

an input button for instructing the measured sound waves to be input and specifying the storage location thereof;

an output button for instructing the measured sound waves, diseases sound waves and examination result to be output;

a speakerphone for outputting the measured sound waves, diseases sound waves and examination result in the form of sound signals;

a display portion for displaying the measured sound waves, disease sound waves and the examination result in accordance with the instruction of the output button; and a controller operating by the operating program, for storing the measured sound waves at a predetermined location of the second memory according to the state of the input button, sequentially outputting the disease sound waves of the third memory to the speakerphone or the display portion according to the state of the output button, and checking whether there is disease sound waves similar to the measured sound waves to extract the examination result regarding the presence or absence of a disease in the examined body to be output to the speakerphone or display portion.

* * * * *